United States Patent
Odom

(10) Patent No.: US 8,357,160 B2
(45) Date of Patent: *Jan. 22, 2013

(54) SYSTEM AND METHOD FOR CONTROLLING ELECTRODE GAP DURING TISSUE SEALING

(75) Inventor: Darren Odom, Longmont, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/411,774

(22) Filed: Mar. 5, 2012

(65) Prior Publication Data

US 2012/0165818 A1   Jun. 28, 2012

Related U.S. Application Data

(63) Continuation of application No. 12/856,722, filed on Aug. 16, 2010, now Pat. No. 8,128,625, which is a continuation of application No. 11/482,886, filed on Jul. 7, 2006, now Pat. No. 7,776,037.

(51) Int. Cl.
   *A61B 18/14* (2006.01)
(52) U.S. Cl. ............................................. 606/51; 606/52
(58) Field of Classification Search .............. 606/50–52, 606/205–209
   See application file for complete search history.

(56) References Cited

U.S. PATENT DOCUMENTS

| 5,431,645 | A  | * | 7/1995 | Smith et al. ....................... 606/1 |
| 7,731,717 | B2 | * | 6/2010 | Odom et al. ..................... 606/51 |
| 7,776,037 | B2 | * | 8/2010 | Odom ............................. 606/51 |
| 8,128,625 | B2 | * | 3/2012 | Odom ............................. 606/51 |
| 2005/0021027 | A1 | * | 1/2005 | Shields et al. .................. 606/51 |
| 2009/0204114 | A1 | * | 8/2009 | Odom ............................. 606/51 |
| 2010/0217264 | A1 | * | 8/2010 | Odom et al. ..................... 606/48 |

* cited by examiner

*Primary Examiner* — Michael Peffley
*Assistant Examiner* — Samantha Good

(57) ABSTRACT

A forceps includes a housing, a shaft, an end effector assembly coupled to the distal end of the shaft and including opposing jaw members, and a drive rod slidingly disposed within the shaft. Each of the jaw members includes a sealing plate attached thereto. Longitudinal reciprocation of the drive rod moves at least one of the jaw members from a first position in spaced relation relative to the other jaw member to at least one subsequent position wherein the sealing plates cooperate to grasp tissue therebetween. The forceps also includes at least one sensor configured to sense a gap distance between the opposing jaw members, and a linear actuator operably coupled to the drive rod. The linear actuator is configured to reciprocate the drive rod in a longitudinal direction as a function of the sensed gap distance in response to signals provided by the at least one sensor.

15 Claims, 9 Drawing Sheets

SYSTEM AND METHOD FOR CONTROLLING ELECTRODE GAP DURING TISSUE SEALING

CROSS-REFERENCE TO RELATED APPLICATIONS

The present application is a continuation application, which claims priority to, and the benefit of, U.S. patent application Ser. No. 12/856,722, filed on Aug. 16, 2010, now U.S. Pat. No. 8,128,625, which is a continuation application that claims priority to, and the benefit of, U.S. patent application Ser. No. 11/482,886, filed on Jul. 7, 2006, now U.S. Pat. No. 7,776,037, the disclosures of which are herein incorporated by reference in their entireties.

BACKGROUND

1. Technical Field

The present disclosure relates to an electrosurgical instrument and method for performing electrosurgical procedures. More particularly, the present disclosure relates to an open or endoscopic bipolar electrosurgical forceps that includes opposing jaw members each having a sealing plate for grasping tissue and supplying electrosurgical energy thereto. The pressure exerted by the sealing plates on the tissue is adjusted using a feedback control loop that utilizes gap distance between the sealing plates as a control variable.

2. Background of Related Art

Electrosurgery involves application of high radio frequency electrical current to a surgical site to cut, ablate, coagulate, cauterize, desiccate or seal tissue. Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

In bipolar electrosurgery, one of the electrodes of the handheld instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

A forceps is a pliers-like instrument that relies on mechanical action between its jaws to grasp, clamp and constrict vessels or tissue. So-called "open forceps" are commonly used in open surgical procedures whereas "endoscopic forceps" or "laparoscopic forceps" are, as the name implies, are used for less invasive endoscopic surgical procedures. Electrosurgical forceps (open or endoscopic) utilize mechanical clamping action and electrical energy to effect hemostasis on the clamped tissue. The forceps includes electrosurgical sealing plates that apply the electrosurgical energy to the clamped tissue. By controlling the intensity, frequency and duration of the electrosurgical energy applied through the sealing plates to the tissue, the surgeon can coagulate, cauterize and/or seal tissue.

Tissue sealing procedures involve more than simply cauterizing tissue. In order to affect a proper seal in vessels or tissue, it has been determined that a variety of mechanical and electrical parameters must be accurately controlled: the pressure applied to the tissue; the gap distance between the electrodes (i.e., distance between opposing jaw members when closed about tissue); and amount of energy applied to tissue.

Numerous electrosurgical instruments have been proposed in the past for various open and endoscopic surgical procedures. However, most of these instruments cauterize or coagulate tissue and are not designed to create an effective or a uniform seal. Other instruments generally rely on clamping pressure alone to procure proper sealing thickness and are often not designed to take into account gap tolerances and/or parallelism and flatness requirements, which are parameters that, if properly controlled, can assure a consistent and effective tissue seal.

SUMMARY

The present disclosure relates to a vessel or tissue sealing instrument that is designed to manipulate, grasp and seal tissue utilizing jaw members. According to one aspect of the present disclosure, an electrosurgical system for sealing tissue is disclosed that includes an electrosurgical forceps. The forceps includes a drive rod and an end effector assembly coupled to the drive rod at a distal end thereof. The end effector assembly includes jaw members wherein longitudinal reciprocation of the drive rod moves the jaw members from a first position in spaced relation relative to one another to a subsequent position wherein the jaw members cooperate to grasp tissue therebetween. Each of the jaw members includes a sealing plate that communicates electrosurgical energy through tissue held therebetween. The jaw members are adapted to connect to an electrosurgical generator. The system also includes one or more sensors that determine a gap distance between the sealing plates of the jaw members and a pressure applicator coupled to the drive rod. The pressure applicator is configured to move the drive rod in a longitudinal direction. The system further includes a controller adapted to communicate with the sensors and to control the pressure applicator in response to the determined gap distance during the sealing process.

The present disclosure also relates to a method for sealing tissue including the step of providing an electrosurgical forceps for sealing tissue. The forceps having at least one shaft member having a drive rod and an end effector assembly mechanically coupled to the drive rod at a distal end thereof. The end effector assembly includes jaw members wherein longitudinal reciprocation of the drive rod moves the jaw members from a first position in spaced relation relative to one another to a subsequent position wherein the jaw members cooperate to grasp tissue therebetween. Each of the jaw members includes a sealing plate that communicates electrosurgical energy through tissue held therebetween. The jaw members are adapted to connect to an electrosurgical generator. The method also includes the steps of providing a controller having a pressure applicator mechanically coupled to the drive rod and configured to move the drive rod in a longitudinal direction as well as grasping tissue between the sealing plates and measuring a gap distance between the sealing plates. The method further includes the step of controlling a pressure applicator as a function of the measured gap distance.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail. Those skilled in the art will understand that the invention according to the present disclosure may be adapted for use with either monopolar or bipolar electrosurgical system.

The present disclosure provides for an apparatus, system and method of controlling pressure exerted by opposing jaw members on tissue grasped therebetween during sealing. Since tissue thickness corresponds to the gap distance "G" between opposing jaw members, it is envisioned that adjusting the pressure exerted on the tissue based on the desired rate of change of the gap distance "G" controls the decrease in the tissue thickness during the sealing process resulting in a confident, more reliable tissue seal. In other words, controlling the rate at which the thickness of the tissue decreases is beneficial in creating a strong seal since the optimum amount of tissue remains enclosed between the opposing jaw members.

Figure 1A:
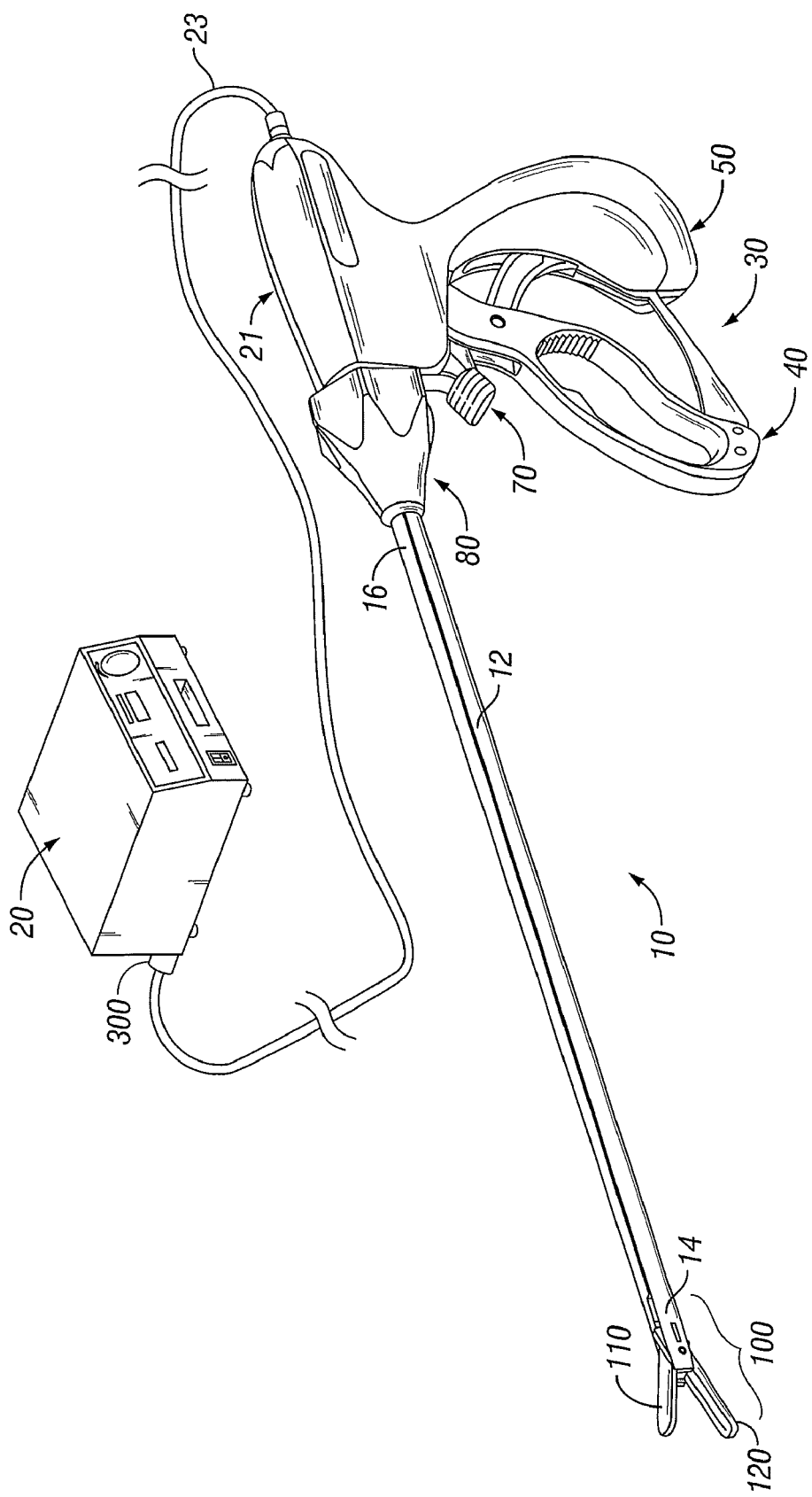
FIG. 1A is a perspective view of an electrosurgical system according to one embodiment of the present disclosure.

FIG. 1A shows an electrosurgical system having an endoscopic vessel sealing bipolar forceps 10 electrically coupled to an electrosurgical generator 20 that is adapted to supply electrosurgical high radio frequency (RF) energy thereto. The forceps 10 is shown by way of example and other suitable electrosurgical forceps are also envisioned that allow control of RF output to provide a reliable seal. Those skilled in the art will understand that the invention according to the present disclosure may be adapted for use with either an endoscopic instrument or an open instrument.

It should also be appreciated that different electrical and mechanical connections and other considerations apply to each particular type of instrument. However, the novel aspects with respect to controlling pressure as a function of the gap distance "G" and the operating characteristics of the instruments remain generally consistent with respect to both the open or endoscopic designs.

Figure 1B:
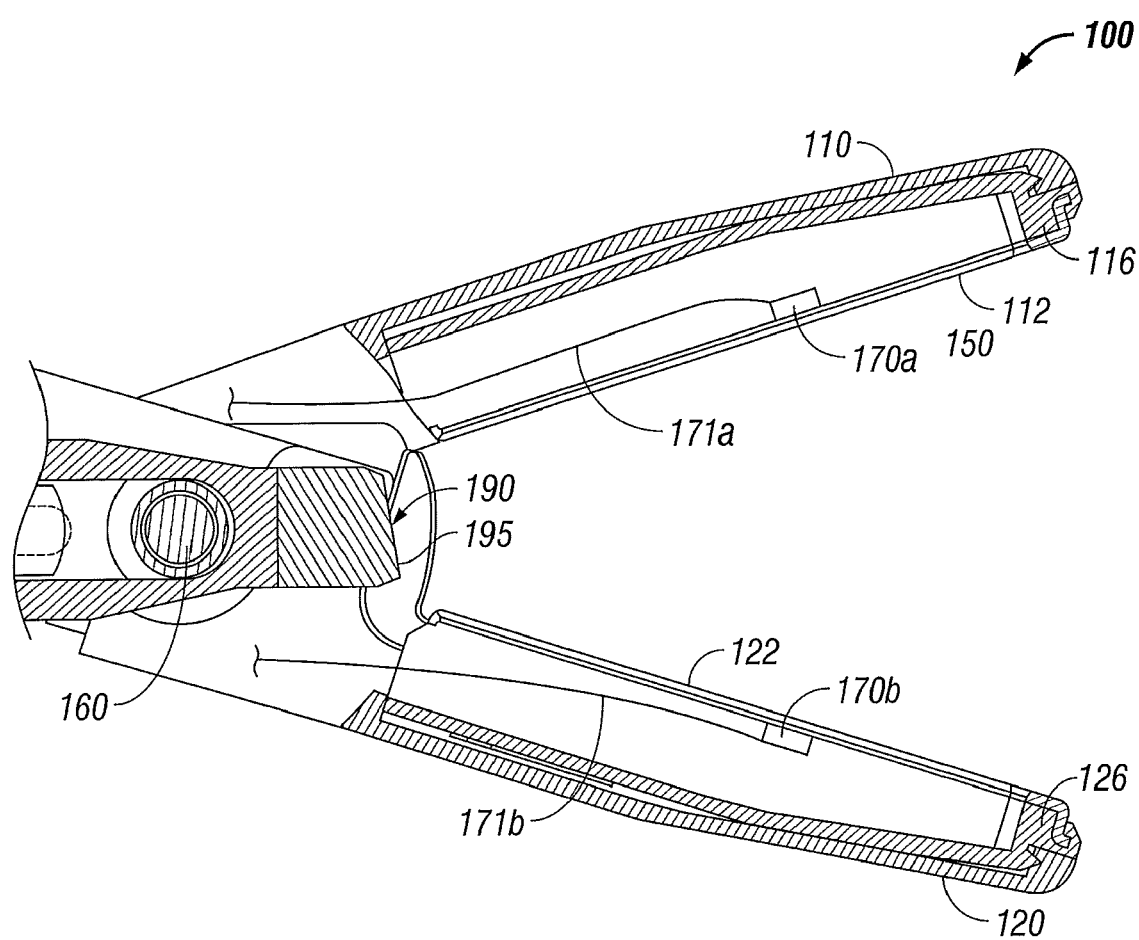
FIG. 1B is a side, partial internal view of an end effector assembly of an endoscopic forceps according to one embodiment of the present disclosure.

FIGS. 1A-1B show the forceps 10 that is configured to support an end effector assembly 100 at a distal end thereof. More particularly, forceps 10 generally includes a housing 21, a handle assembly 30, a rotating assembly 80, and a trigger assembly 70 that mutually cooperate with the end effector assembly 100 to grasp, seal and, if desired, divide tissue.

The forceps 10 also includes a shaft 12 that has a distal end 14 that mechanically engages the end effector assembly 100 and a proximal end 16 that mechanically engages the housing 21 proximate the rotating assembly 80. In the drawings and in the description that follows, the term "proximal", refers to the end of the forceps 10 that is closer to the user, while the term "distal" refers to the end of the forceps that is further from the user.

Figure 2:
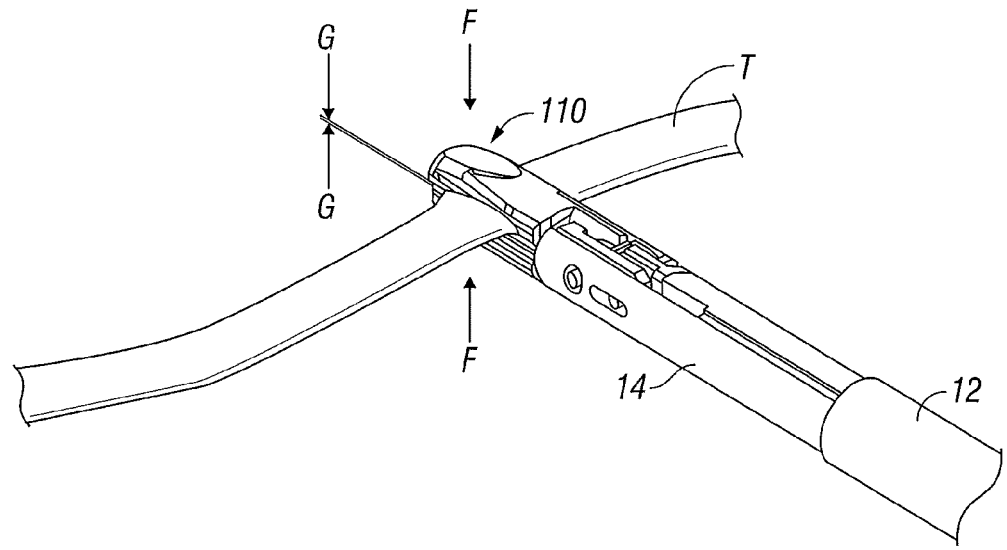
FIG. 2 is a rear, perspective view of the end effector of FIG. 1B shown with tissue grasped therein.

The forceps 10 also includes a plug 300 that connects the forceps 10 to a source of electrosurgical energy, e.g., the electrosurgical generator 20, via an electrical cable 23. Handle assembly 30 includes a fixed handle 50 and a movable handle 40. Handle 40 moves relative to the fixed handle 50 to actuate the end effector assembly 100 and enables a user to grasp and manipulate tissue "T" as shown in FIG. 2.

The generator 20 includes input controls (e.g., buttons, activators, switches, touch screen, etc.) for controlling the generator 20. In addition, the generator 20 may include one or more display screens for providing the surgeon with a variety of output information (e.g., intensity settings, treatment completion indicators, etc.). The controls allow the surgeon to adjust the RF energy, waveform, and other parameters to achieve the desired waveform suitable for a particular task (e.g., coagulating, tissue sealing, intensity setting, etc.). The forceps 10 may also include a plurality of input controls that may be redundant with certain input controls of the generator 20. Placing the input controls at the forceps 10 allows for easier and faster modification of RF energy parameters during the surgical procedure without requiring interaction with the generator 20.

Figure 3:
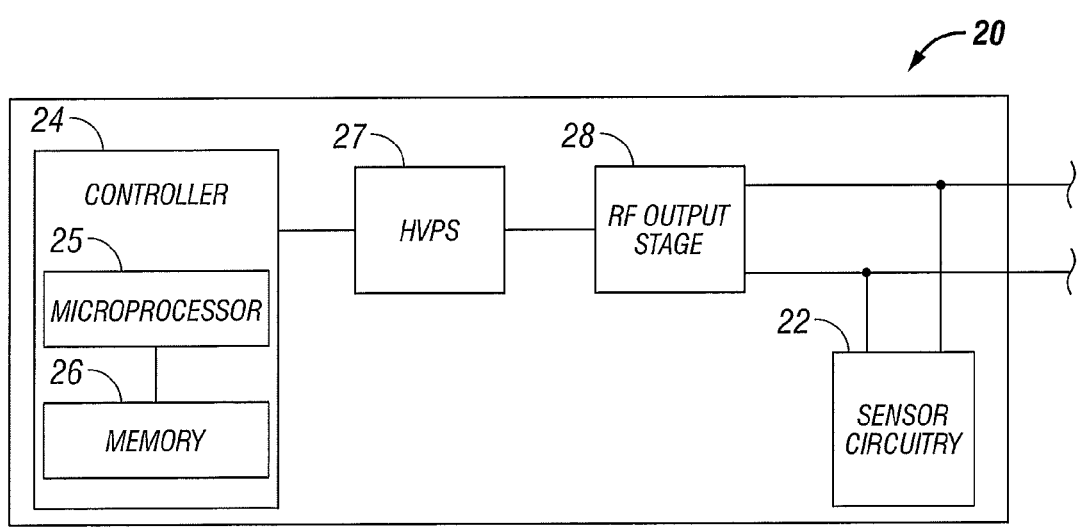
FIG. 3 is a schematic block diagram of a generator system according to one embodiment of the present disclosure.

FIG. 3 shows a schematic block diagram of the generator 20 having a controller 24, a high voltage DC power supply 27 ("HVPS") and an RF output stage 28. The HVPS 27 provides high voltage DC power to RF output stage 28, which then converts high voltage DC power into RF energy and delivers the RF energy to an active electrode. In particular, the RF output stage 28 generates sinusoidal waveforms of high frequency RF energy. The RF output stage 28 is configured to generate a plurality of suitable waveforms having various duty cycles, peak voltages, crest factors, and other parameters. Certain types of waveforms are suitable for specific electrosurgical modes. For instance, the RF output stage 28 generates a 100% duty cycle sinusoidal waveform in a so called "cut mode," which is best suited for dissecting tissue and a 25% duty cycle waveform in a so called "coagulation mode," which is best used for cauterizing tissue to stop bleeding.

The controller 24 includes a microprocessor 25 connected to a memory 26, which may be volatile type memory (e.g., RAM) and/or non-volatile type memory (e.g., flash media, disk media, etc.). The microprocessor 25 includes an output port that is connected to the HVPS 27 and/or RF output stage 28 allowing the microprocessor 25 to control the output of the generator 20 according to either open and/or closed control loop schemes.

The sensor circuitry 22 may include a plurality of sensors for measuring a variety of tissue and/or energy properties (e.g., tissue impedance, tissue temperature, output current and/or voltage, gap distance, etc.). The sensor circuitry 22 is also connected to sensors 170a and 170b, which measure the gap distance "G" between the opposing jaw members 110 and 120 (FIG. 1B). Such sensors are within the purview of those skilled in the art. A closed loop control scheme is a feedback control loop wherein sensor circuitry 22 provides feedback to the controller 24. The controller 24 signals the HVPS 27 and/or RF output stage 28, which then adjusts the output of DC and/or RF energy, respectively. The sensor circuitry 22 also transmits measured gap distance "G" information to the controller 24, which then adjusts the pressure exerted by the opposing jaw members 110 and 120 exerted on the tissue grasped therein. The controller 24 also receives input signals from the input controls of the generator 20 or the forceps 10. The controller 24 utilizes the input signals to adjust power outputted by the generator 20 and/or performs other suitable control functions thereon.

With references to FIGS. 1A-1B, the end effector assembly 100 includes a pair of opposing jaw members 110 and 120 each having an electrically conductive sealing plate 112 and 122, respectively, attached thereto for conducting electrosurgical energy through tissue "T" held therebetween. More particularly, the jaw members 110 and 120 move in response to movement of the handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto.

The jaw members 110 and 120 are activated using a drive assembly (not explicitly shown) enclosed within the housing 21. The drive assembly cooperates with the movable handle 40 to impart movement of the jaw members 110 and 120 from the open position to the clamping or closed position. Examples of handle assemblies are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS".

In addition, the handle assembly 30 of this particular disclosure may include a four-bar mechanical linkage, which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. Movable handle 40 of handle assembly 30 is ultimately connected to a drive rod 32 that, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Figure 1C:
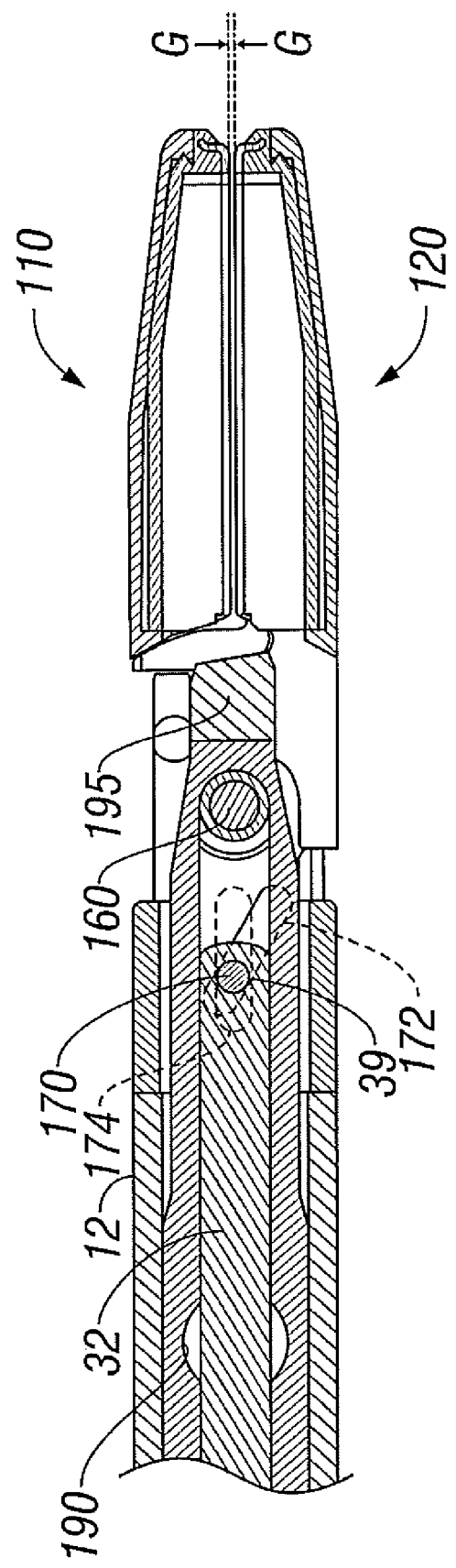
FIGS. 1C-1E are side, partial internal views of an end effector assembly of FIG. 1B with pressure application mechanisms according to various embodiments of the present disclosure.

As best illustrated in FIG. 1C, drive rod 32 includes a pin slot 39 disposed at the distal tip of the drive rod 32 and dimensioned to house the cam pin 170 such that longitudinal reciprocation of the drive rod 32 translates the cam pin 170, which, in turn, rotates the jaw members 110 and 120 about pivot pin 160. The cam pin 170 rides within slots 172 and 174 of the jaw members 110 and 120, respectively, which causes the jaw members 110 and 120 to rotate from the open to closed positions about the tissue. In particular, as the drive rod 32 is pulled proximally the cam pin 170 is moved proximally within cam slots 172 and 174 and closes the jaw members 110 and 120 relative to one another. The drive rod 32 is configured to be actuated via the handle 40 and/or other suitable pressure application mechanisms.

Figure 1D:
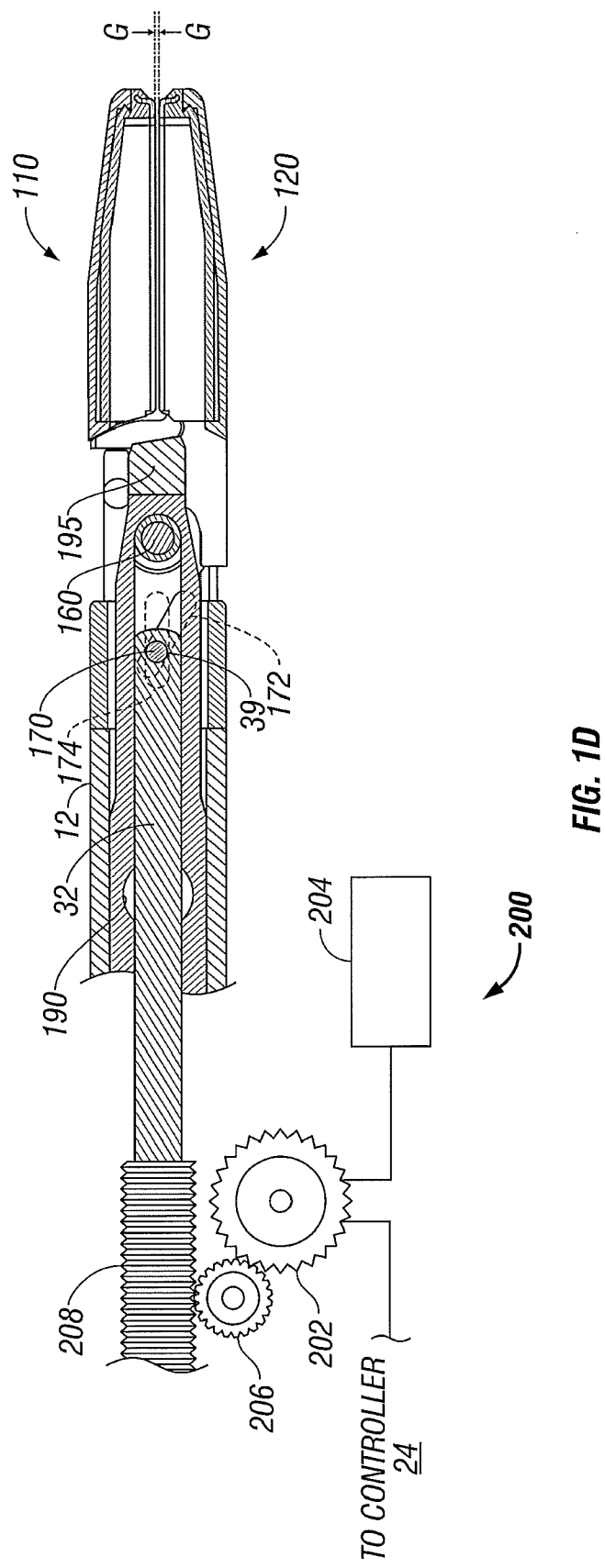

FIG. 1D shows a motor-controlled pressure applicator 200 that includes an electric motor 202 powered by a power source 204. The power source 204 may either be a stand-alone low voltage DC source (e.g., battery) or an integrated low-voltage power source as part of the HVPS 27. The drive rod 32 includes a threaded portion 208 that is in mechanical communication with the motor 202. In particular, the motor 202 includes a gear box 206 that is mechanically coupled to the threaded portion 208 so that when the motor 202 is activated, the gears of the gear box 206 rotate and thereby longitudinally move the drive rod 32. Pulling the drive rod 32 proximally and moving the jaw members 110 and 120 apart or pushing the drive rod 32 distally and moving the jaw members 110 and 120 together is accomplished by varying the direction of rotation of the motor 202. The rate of closure of the jaw members 110 and 120 is controlled by varying the gears within the gear box 206 and/or the power supplied to the motor 202, which, in turn, adjusts the rate of rotation and torque exerted on the drive rod 32. Control of the motor 202 is achieved via the controller 24, which automatically adjusts the operating parameters thereof based on user input or sensed feedback from the sensor circuitry 22 and/or the sensors 170a and 170b.

Figure 1E:
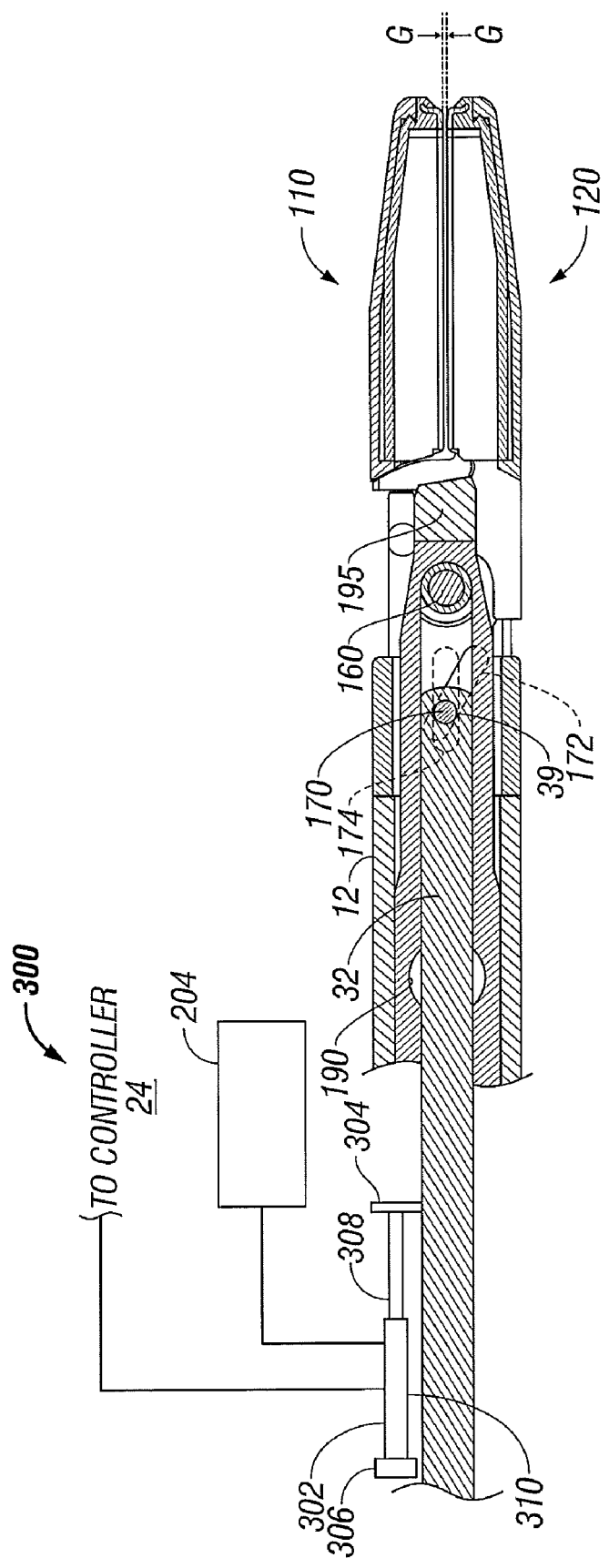

FIG. 1E shows another embodiment of a pressure applicator 300 that includes a linear actuator 302 powered by the power source 204. The linear actuator 302 includes a housing cylinder 310 and a shaft 308. The shaft 308 is mechanically coupled to the drive rod 32 at an interface 304 and the housing cylinder 310 is mechanically coupled to the interior wall of the housing 21 at an interface 306. The linear actuator 302 moves the drive rod 32 in a longitudinal direction proximally or distally by expanding or contracting, respectively, between the interfaces 304 and 306. The linear actuator 302 includes either an electric motor or a pneumatic or hydraulic cylinders that extend or retract the shaft 308. Those skilled in the art will readily appreciate that if the linear actuator 302 is pneumatic, the shaft 308 may be part of the pneumatic cylinder. The power source 204 is connected to the linear actuator 302 and provides electrical power thereto. The controller 24 controls the operating parameters of the linear actuator 302 either directly or by controlling the power source 202 based on user input or sensed feedback from the sensor circuitry 22 and/or the sensors 170a and 170b.

The pressure applicators 200 and 300 may be housed within the housing 21 or outside thereof along the shaft 12 to enable the pressure applicators 200 and 300 to interface with drive rod 32.

The details relating to the inter-cooperative relationships of the inner-working components of forceps 10 are disclosed in the above-cited commonly-owned U.S. patent application Ser. No. 10/369,894. Another example of an endoscopic handle assembly that discloses an off-axis, lever-like handle assembly, is disclosed in the above-cited U.S. patent application Ser. No. 10/460,926.

Referring back to FIGS. 1A-1B, the forceps 10 also includes a trigger 70 that advances a knife 190 disposed within the end effector assembly 100. Once a tissue seal is formed, the user optionally activates the trigger 70 to separate the tissue "T" along the tissue seal. Knife 190 preferably includes a sharpened edge 195 for severing the tissue "T" held between the jaw members 110 and 120 at the tissue sealing site. The knife 190 longitudinally reciprocates in a longitudinally-oriented channel (not explicitly shown) defined in the conductive sealing plates 112 and 122 extending from the proximal end to the distal end thereof. The channel facilitates longitudinal reciprocation of the knife 190 along a preferred cutting plane to effectively and accurately separate the tissue "T" along a formed tissue seal.

The forceps 10 also includes a rotating assembly 80 mechanically associated with the shaft 12 and the drive assembly (not explicitly shown). Movement of the rotating assembly 80 imparts similar rotational movement to the shaft 12, which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1A-1B, the end effector assembly 100 attaches to the distal end 14 of shaft 12. The jaw members 110 and 120 are preferably pivotable about a pivot 160 from the open to closed positions upon relative reciprocation, i.e., longitudinal movement, of the drive assembly (not explicitly shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

The forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 21 and handle assembly 30. In either of these two instances, the forceps 10 may be either partially disposable or reposable, such as where a new or different end effector assembly 100 or end effector assembly 100 and shaft 12 are used to selectively replace the old end effector assembly 100 as needed.

Since the forceps 10 applies energy through electrodes, each of the jaw members 110 and 120 includes an electrically conductive sealing plate 112 and 122, respectively, disposed on an inner-facing surface thereof. Thus, once the jaw members 110 and 120 are fully compressed about the tissue T, the forceps 10 is now ready for selective application of electrosurgical energy as shown in FIG. 2. At that point, the electrically conductive plates 112 and 122 cooperate to seal tissue "T" held therebetween upon the application of electrosurgical energy. Jaw members 110 and 120 also include insulators 116 and 126, which together with the outer, non-conductive plates of the jaw members 110 and 120 are configured to limit and/or reduce many of the known undesirable effects related to tissue sealing, e.g., flashover, thermal spread and stray current dissipation as shown in FIG. 1B.

The gap distance "G" is used as a sensed feedback to control the thickness of the tissue being grasped. More particularly, a pair of opposing sensors 170a and 170b are configured to provide real-time feedback relating to the gap distance between the sealing plates 112 and 122 of the jaw members 110 and 120 during the sealing process via electrical connection 171a and 171b, respectively. The sensors 170a and 170b provide sensed feedback to the sensor circuitry 22, which then signals the controller 24. The controller 24 then signals the pressure applicator to adjust the pressure applied to the tissue based on the measured gap distance "G." Consequently, this controls the rate at which tissue grasped between the sealing plates 112 and 122 is being compressed.

The sensors 170a and 170b may be any suitable sensors, such as laser distancers, LED distancers, optical encoders, and the like. The laser and LED distancers operate by bouncing light beams from an opposing surface and measuring the duration of the beam of light to travel back to the sensors 170a and 170b. The sensors 170a and 170b bounce light beams from the opposing surfaces (e.g., sealing plates 112 and 122).

Each of the sensors 170a and 170b provides an individual measurement of the distance between the jaw members 110 and 120. An optical encoder (e.g., a linear encoder) is a sensor paired with a scale (not explicitly shown) that corresponds to a particular position of the jaw members 110 and 120. The sensor 170a reads the scale and converts the encoded position into an analog or digital signal, which can then be decoded into position by a digital readout (e.g., sensor circuitry 22). Motion of the jaw members 110 and 120 is determined by change in position over time. Linear encoder technologies include capacitive, inductive, eddy current, magnetic, and optical. Optical technologies include shadow, self imaging and interferometric. The sensor circuitry 22 and/or the controller 24 then average the result to arrive at the gap distance "G" separating the jaw members 110 and 120. The sensor circuitry 22 and/or the controller 24 may perform various other types of calculations based on the gap distance "G" measurements to obtain desired empirical values for sensed feedback control.

The sensors 170a and 170b may also be configured to measure suitable tissue properties, such as tissue impedance and temperature. Such sensors are within purview of those skilled in the art.

The gap distance "G" is directly related to the thickness of tissue being grasped between the sealing plates 112 and 122. Therefore, the thickness of tissue being grasped may be controlled based on the gap distance "G." As shown in a graph of FIG. 5, thickness of the tissue (and therefore the gap distance "G") decreases as pressure and energy are applied thereto. Tissue thickness decreases for at least two reasons. First, the pressure applied to the tissue by the sealing plates 112 and 122 compresses tissue. Second, RF energy applied to the tissue increases the temperature therein at which point intracellular fluids being to boil thereby causing the cells to rupture uncontrollably.

Figure 5:
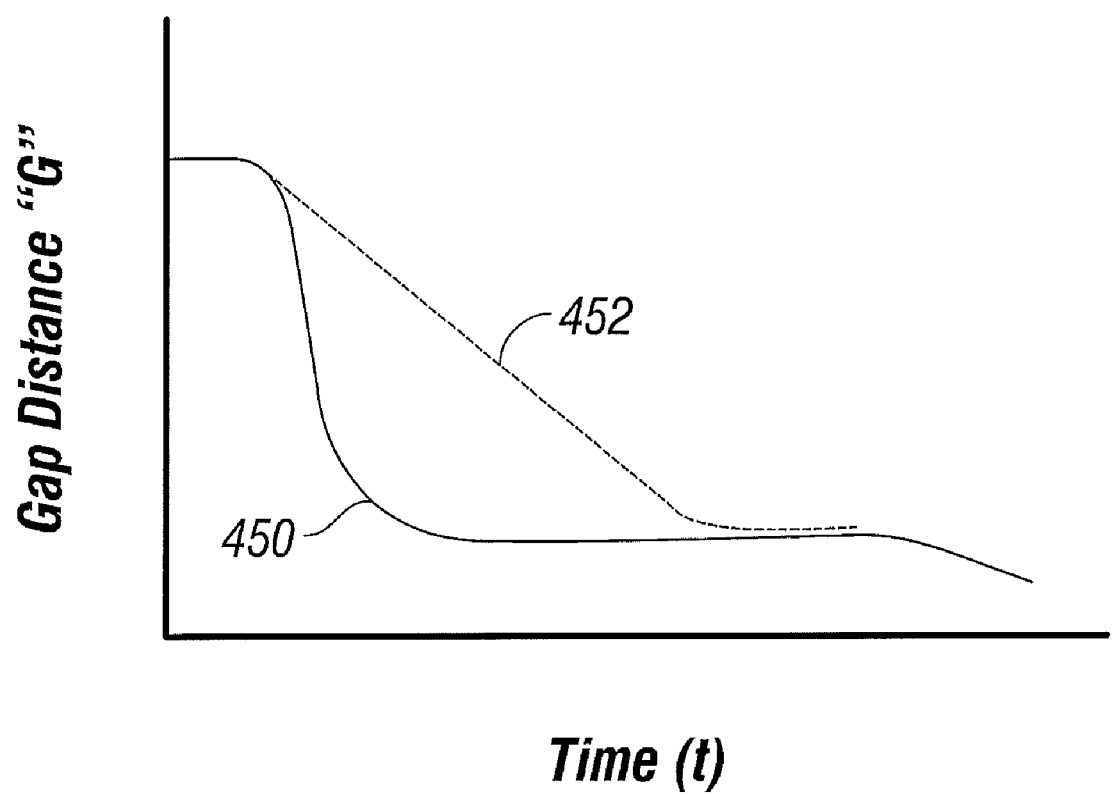
FIG. 5 shows a graph of gap distance "G" versus time (t) utilizing the method of FIG. 4.

The graph of FIG. 5 shows a plot 450 of gap distance "G" between electrode plates of a conventional electrosurgical sealing forceps where RF energy is supplied at a constant rate and pressure is unregulated. In the plot 450, the gap distance "G" falls to approximately half of the original value very quickly (e.g., approximately 0.5 seconds). This demonstrates as pressure and energy are applied at a constant rate during initial stages of a sealing procedure, thickness of the tissue rapidly decreases as the tissue is being cooked.

Plot 452 shows a more desirable progression of the gap distance "G." In particular, if the thickness of the tissue decreases at a more controlled rate the mucosa and submucosa tissues remain in the seal area. Conventionally, the mucosa and submucosa layers are pressed out of the seal area due to uncontrolled delivery of RF energy, resulting in a less secure seal. Therefore, the controlled decrease of the gap distance "G" of the plot 452 allows for controlled decreases of the tissue thickness. This may be accomplished by controlling pressure as a function of the gap distance "G." More specifically, an embodiment of the present disclosure controls application of pressure to tissue during sealing based on the gap distance "G" to maintain the desired rate of cell rupture, thereby controlling the thickness of the tissue being grasped.

Figure 4:
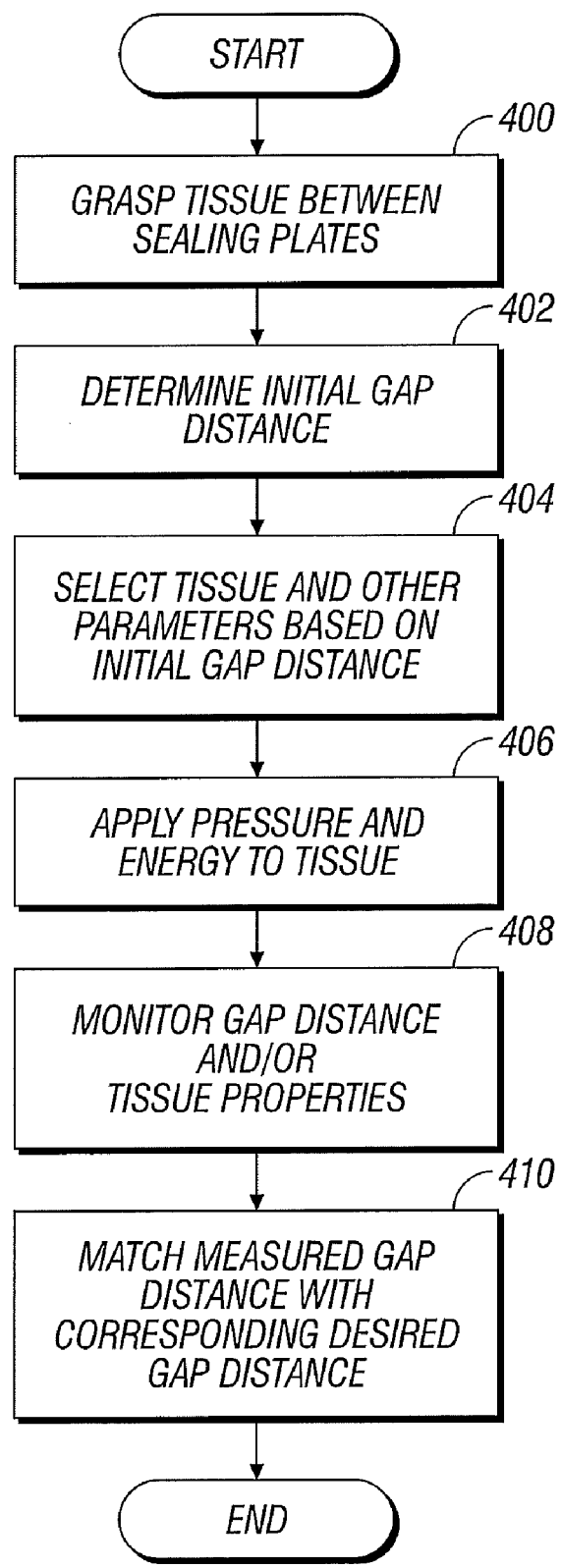
FIG. 4 is a flowchart showing a sealing method using a bipolar forceps according to a method of the present disclosure.

A sealing method according to one embodiment of the present disclosure is shown in FIG. 4. In step 400, the forceps 10 grasps the tissue "T" using the jaw members 110 and 120. The sealing plates 112 and 122 are activated and are in contact with the tissue "T" but are not fully closed. When the sealing plates 112 and 122 contact the tissue "T" electrosurgical energy is applied thereto and the collagen contained therein is denatured and becomes more mobile (i.e., liquefies).

In step 402, initial gap distance "G" is determined by sensors 170a, 170b, which measure the distance between jaw members 110 and 120. The initial gap distance "G" measurement is useful in determining the thickness of the tissue being grasped. The thickness is particularly important since various adjustments to the procedure may be made based on relative tissue thickness. For instance, thin tissue types (e.g., small blood vessels) may require a certain amount of energy and pressure to properly seal desiccation whereas thicker tissue types may require more pressure and more energy. Other tissue parameters may be used to determine thickness and/or properties of the tissue. A second sensor or one of the sensors 170a and 170b may be adapted to measure boundary conditions, jaw fill, hydration. This may be accomplished by using optical sensors adapted to measure opacity of the tissue. The tissue property measurements are transmitted to the controller 24 through the sensor circuitry 22, wherein adjustments to the generator 20 and the pressure applicator are made in real-time based on the measurements.

In step 404, energy, tissue and other treatment parameters are selected. More specifically, the initial gap distance "G" measurement is transmitted to the controller 24 where the tissue thickness is determined as a function thereof. The determination may be accomplished by matching the measured initial gap distance "G" with gap distance "G" values stored in a look-up table stored in memory 26. The look-up table may include a plurality of gap distance "G" values and corresponding tissue thickness values. Upon finding a match, corresponding tissue thickness is obtained. In addition, the look-up table may also include suitable energy and pressure parameters associated with the corresponding tissue thickness. Energy and pressure parameters may also be loaded based on the initial gap distance "G" determination without determining the tissue thickness.

In step 406, the forceps 10 begins to apply pressure and energy to the tissue "T" using the jaw members 110 and 120 based on the energy and pressure parameters loaded in step 504. The pressure may be constant or be applied to according to a desired pattern (e.g., a control curve). The desired gap distance "G" may be expressed as a desired gap distance "G" trajectory, namely, plot 452. The gap distance trajectory "G" includes a plurality of desired gap distance "G" values. The look-up table may include a plurality of parameters, such as starting and ending gap distances "G," desired slope(s), etc. The microprocessor 25 uses these parameters to construct the plot 452 (i.e., the desired trajectory), which may be linear, quasi-linear, or non-linear. The gap distance "G" may also be controlled according to preset parameters and time increments based on pre-existing empirical data and not in real-time according to real changes in gap distance "G."

In step 408, as RF energy and pressure are applied to tissue, gap distance "G" is continually monitored and compared with the plot 452 in particular with corresponding desired gap distance "G" values. The gap distance "G" may also be controlled based in response to other tissue properties, such as tissue impedance and temperature. Impedance and temperature are continually monitored along with the gap distance "G" and are transmitted by the sensors 170a and 170b to the controller 24 wherein the controller 24 makes appropriate adjustments to the pressure applicator to control the pressure.

In step 410, the controller 24 adjusts the pressure based on the measured gap distance "G" or other tissue properties by matching measured gap distance "G" with desired gap distance "G." This is accomplished at specific time increments, which may be predetermined or dynamically defined. Namely, for every time increment, measured gap distance "G" is compared with a corresponding desired gap distance "G." If the measured gap distance drops off rapidly and is below the desired corresponding gap distance "G" value of the plot 452, the controller 24 adjusts pressure output of the pressure applicator (e.g., lowers the pressure).

An apparatus and method according to the present disclosure allow for tissue sealing procedures that retain the collagen at the sealing site, which is known to enhance the consistency, effectiveness, and strength of tissue seals. This may be accomplished by using a "slow close" activation to initially denature the collagen and then close the sealing plates under pressure at a predetermined rate. Further details relating to "slow close" activation are disclosed in commonly-owned U.S. application Ser. No. 11/095,123 filed Mar. 31, 2005 entitled "ELECTROSURGICAL FORCEPS WITH SLOW CLOSURE SEALING PLATES AND METHOD OF SEALING TISSUE", which is herein incorporated by reference. This allows for limited extrusion of the cured and mixed collagen mass from the sealing site, which contributes to an effective and uniform seal.

Figure 6:
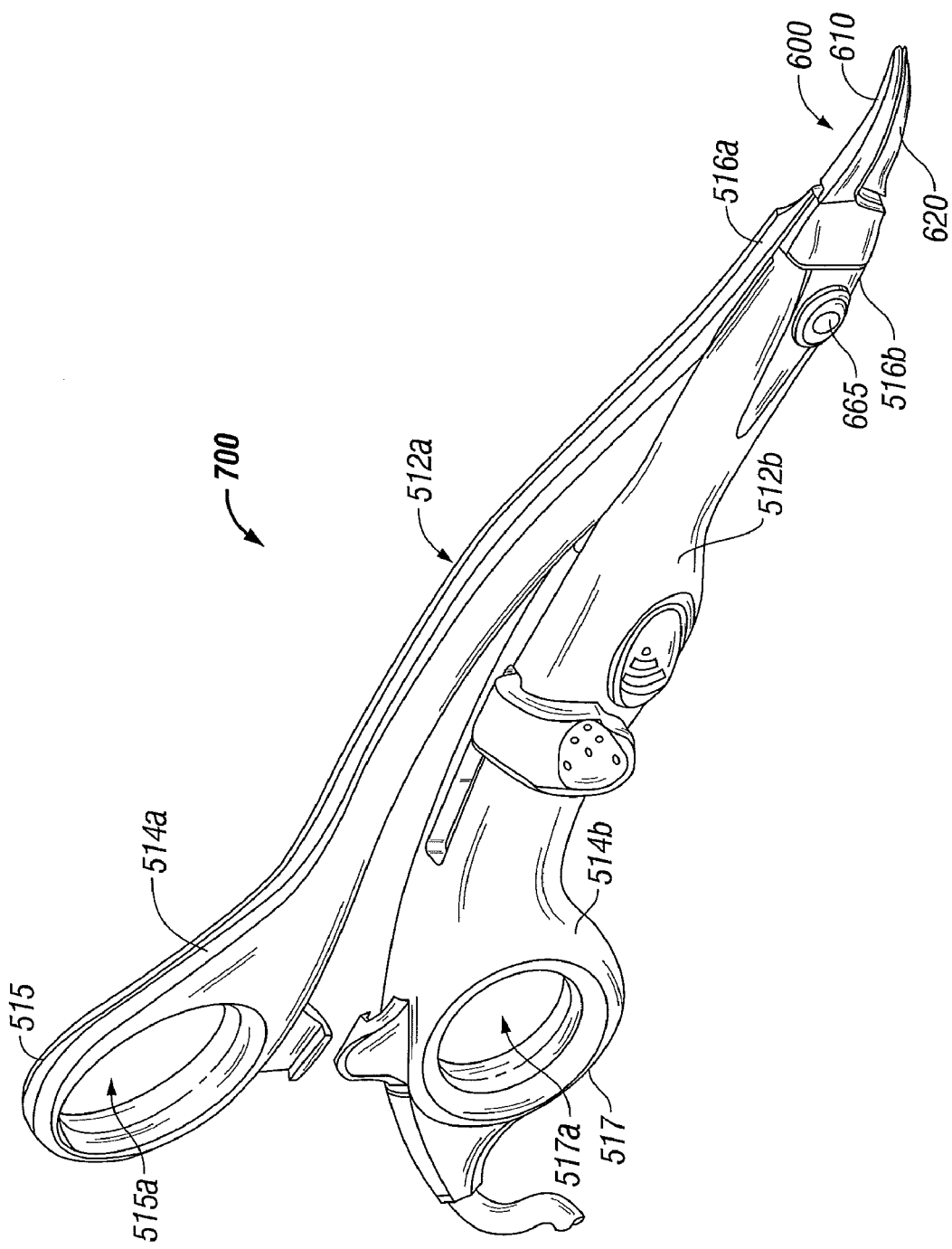
FIG. 6 is a perspective view of an open bipolar forceps that is configured to close at a predetermined rate according to one embodiment of the present disclosure.

From the foregoing and with reference to the various figure drawings, those skilled in the art will appreciate that certain modifications can also be made to the present disclosure without departing from the scope of the same. For example and as mentioned above, any of the slow closure techniques, methods and mechanisms disclosed herein may be employed on an open forceps such as the open forceps 700 disclosed in FIG. 6. The forceps 700 includes an end effector assembly 600 that attaches to the distal ends 516a and 516b of shafts 512a and 512b, respectively. The end effector assembly 600 includes pair of opposing jaw members 610 and 620 that are pivotally connected about a pivot pin 665 and are movable relative to one another to grasp vessels and/or tissue. Stop member assemblies, such as those described with respect to FIGS. 1A-1B, 3 and 4, and sensors 170a and 170b may be disposed within the end effector 600 to regulate the RF energy according to real-time measurements and changes to the gap distance "G" during sealing.

Each shaft 512a and 512b includes a handle 515 and 517, respectively, disposed at the proximal end 514a and 514b thereof each of the handles 515 and 517 define a finger hole 515a and 517a, respectively, therethrough for receiving a finger of the user. Finger holes 515a and 517a facilitate movement of the shafts 512a and 512b relative to one another, which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT".

In addition, the presently disclosed forceps may include an electrical cutting configuration to separate the tissue either prior to, during or after cutting. One such electrical configuration is disclosed in commonly-assigned U.S. patent application Ser. No. 10/932,612 entitled "VESSEL SEALING INSTRUMENT WITH ELECTRICAL CUTTING MECHANISM," which is herein incorporated by reference.

Moreover, only one sensor in one jaw member may be utilized to measure the initial and real-time changes in the gap distance "G." The sensor may be configured to provide an initial gap distance value to the microprocessor or generator, which enables a predetermined starting gap distance value, trajectory and ending gap distance value.

In addition, the gap distance "G" may be selectively regulated by adjusting one or more stop members that extend from the tissue sealing surfaces. Several configurations of this feature are shown in a commonly-owned U.S. patent application Ser. No. 10/846,262 entitled "TISSUE SEALER WITH NON-CONDUCTIVE VARIABLE STOP MEMBERS AND METHOD OF SEALING TISSUE," which is herein incorporated by reference.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
a housing;
a shaft including a distal end and a proximal end, the proximal end associated with the housing;
an end effector assembly coupled to the distal end of the shaft and including opposing jaw members, wherein each of the jaw members includes a sealing plate attached thereto;
a drive rod slidingly disposed within the shaft, wherein longitudinal reciprocation of the drive rod moves at least one of the jaw members from a first position in spaced relation relative to the other jaw member to at least one subsequent position wherein the sealing plates cooperate to grasp tissue therebetween;
at least one sensor configured to sense a gap distance between the opposing jaw members; and
a linear actuator operably coupled to the drive rod, the linear actuator configured to reciprocate the drive rod in a longitudinal direction as a function of the sensed gap distance in response to signals provided by the at least one sensor.

2. The forceps as in claim 1, wherein the linear actuator is disposed within the housing.

3. The forceps as in claim 1, wherein the linear actuator is disposed along the shaft, the shaft adapted to enable the linear actuator to interface with the drive rod.

4. The forceps as in claim 1, wherein each sealing plate is adapted to connect to an electrosurgical energy source and is configured to communicate electrosurgical energy through tissue grasped therebetween.

5. The forceps as in claim 1, wherein the at least one sensor is disposed within the end effector assembly.

6. A forceps, comprising:
a housing;
a shaft including a distal end and a proximal end, the proximal end associated with the housing;
an end effector assembly coupled to the distal end of the shaft and including opposing jaw members, wherein each of the jaw members includes a sealing plate attached thereto;
a drive rod slidingly disposed within the shaft, wherein longitudinal reciprocation of the drive rod moves at least one of the jaw members from a first position in spaced relation relative to the other jaw member to at least one subsequent position wherein the sealing plates cooperate to grasp tissue therebetween;
at least one sensor configured to sense a gap distance between the opposing jaw members; and
a linear actuator operably coupled to the drive rod, the linear actuator configured to reciprocate the drive rod in a longitudinal direction as a function of the sensed gap distance in response to control signals received from a controller communicatively coupled to the at least one sensor.

7. The forceps as in claim 6, wherein the linear actuator is disposed within the housing.

8. The forceps as in claim 6, wherein the linear actuator is disposed along the shaft, the shaft adapted to enable the linear actuator to interface with the drive rod.

9. The forceps as in claim 6, wherein each sealing plate is adapted to connect to an electrosurgical energy source and is configured to communicate electrosurgical energy through tissue grasped therebetween.

10. The forceps as in claim 6, wherein the at least one sensor is disposed within the end effector assembly.

11. An electrosurgical system, comprising:
a housing;
a shaft including a distal end and a proximal end, the proximal end associated with the housing;
an end effector assembly coupled to the distal end of the shaft and including opposing jaw members, wherein each of the jaw members includes a sealing plate attached thereto;
a drive rod slidingly disposed within the shaft, wherein longitudinal reciprocation of the drive rod moves at least one of the jaw members from a first position in spaced relation relative to the other jaw member to at least one subsequent position wherein the sealing plates cooperate to grasp tissue therebetween;
at least one sensor configured to sense a gap distance between the opposing jaw members;
a linear actuator operably coupled to the drive rod, the linear actuator configured to reciprocate the drive rod in a longitudinal direction; and
a controller operable to communicate with the at least one sensor to control the linear actuator as a function of the sensed gap distance in order to control the reciprocation of the drive rod and resultant pressure between the jaw members.

12. The electrosurgical system as in claim 11, wherein the linear actuator is disposed within the housing.

13. The electrosurgical system as in claim 11, wherein the linear actuator is disposed along the shaft, the shaft adapted to enable the linear actuator to interface with the drive rod.

14. The electrosurgical system as in claim 11, wherein each sealing plate is adapted to connect to an electrosurgical energy source and is configured to communicate electrosurgical energy through tissue grasped therebetween.

15. The electrosurgical system as in claim 11, wherein the at least one sensor is disposed within the end effector assembly.

* * * * *